(12) United States Patent
Bindefeld

(10) Patent No.: US 7,393,326 B2
(45) Date of Patent: Jul. 1, 2008

(54) APPARATUS FOR SCREENING AND DIAGNOSING BY DUAL STETHOSCOPIC AND DOPPLER DETECTION

(76) Inventor: Herve Bindefeld, 7, rue des Acacias, Paris (FR) F-75017

( * ) Notice: Subject to any disclaimer, the term of this patent is extended or adjusted under 35 U.S.C. 154(b) by 541 days.

(21) Appl. No.: 10/508,990

(22) PCT Filed: Mar. 27, 2003

(86) PCT No.: PCT/FR03/00972

§ 371 (c)(1), (2), (4) Date: Sep. 27, 2004

(87) PCT Pub. No.: WO03/079904

PCT Pub. Date: Oct. 2, 2003

(65) Prior Publication Data

US 2005/0165310 A1  Jul. 28, 2005

(30) Foreign Application Priority Data

Mar. 27, 2002 (FR) .................................. 02 03833
Sep. 9, 2002 (FR) .................................. 02 11152

(51) Int. Cl.
*A61B 8/00* (2006.01)
(52) U.S. Cl. ........................... 600/453; 381/67; 181/131
(58) Field of Classification Search ................. 600/453, 600/454, 437; 181/131; 381/67
See application file for complete search history.

(56) References Cited

U.S. PATENT DOCUMENTS 4,413,629 A * 11/1983 Durley, III .................. 600/453
4,986,276 A * 1/1991 Wright ....................... 600/454
5,052,395 A * 10/1991 Burton et al. ................ 600/455
5,135,001 A * 8/1992 Sinofsky et al. ............. 600/459
5,390,679 A * 2/1995 Martin ....................... 600/486
5,630,418 A * 5/1997 Lee et al. .................... 600/453
5,644,177 A * 7/1997 Guckel et al. .......... 310/40 MM
5,662,116 A * 9/1997 Kondo et al. ................ 600/462
5,960,089 A * 9/1999 Bouricius et al. ............. 381/67
5,964,709 A   10/1999 Chiang et al.
5,984,889 A * 11/1999 Christ et al. .................. 604/22
6,086,539 A * 7/2000 Guracar et al. .............. 600/453
6,626,837 B2 * 9/2003 Muramatsu et al. ......... 600/459
2002/0049374 A1 * 4/2002 Abreu ........................ 600/405

* cited by examiner

Primary Examiner—Eric F. Winakur
Assistant Examiner—Katherine L Fernandez
(74) Attorney, Agent, or Firm—Dickinson Wright, PLLC

(57) ABSTRACT

The invention concerns an apparatus for early screening of cardiovascular diseases through dual stethoscopic and Doppler detection with means ensuring coherence between the two types of detection. According the invention, the medical screening and diagnosis apparatus comprises a sound transmitting linking conduit (3, 33) connected, on one end, to a housing (100) forming at least partly an ear trumpet (1') provided with a membrane (2), and, on the other end, at least an earphone (4) for listening to a stethoscopic signal from the ear trumpet (1'). The invention is characterized in that the housing (100) of the apparatus contains at least an ultrasound probe (8) designed to enable convergence of reception of the ultrasonic and stethoscopic signals. The probe is connected to a transducer processing circuit (37) capable of supplying, from a Doppler signal, an audio signal by coupling the processing circuit to a loudspeaker (34) in contact with the ear trumpet for stethoscopic-type listening, and a video signal by coupling the processing circuit (37) to display means (39) to provide visual information.

45 Claims, 12 Drawing Sheets

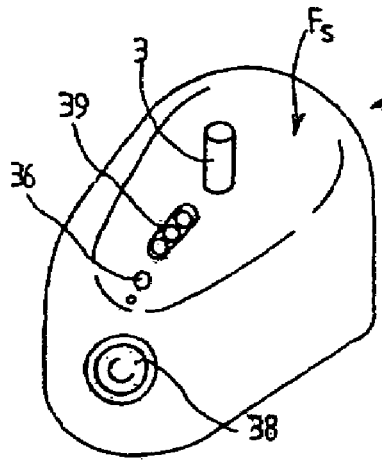
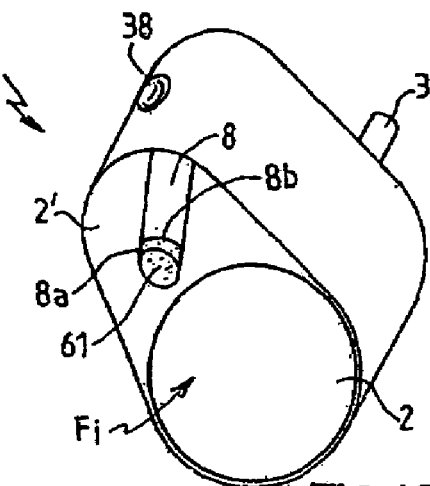
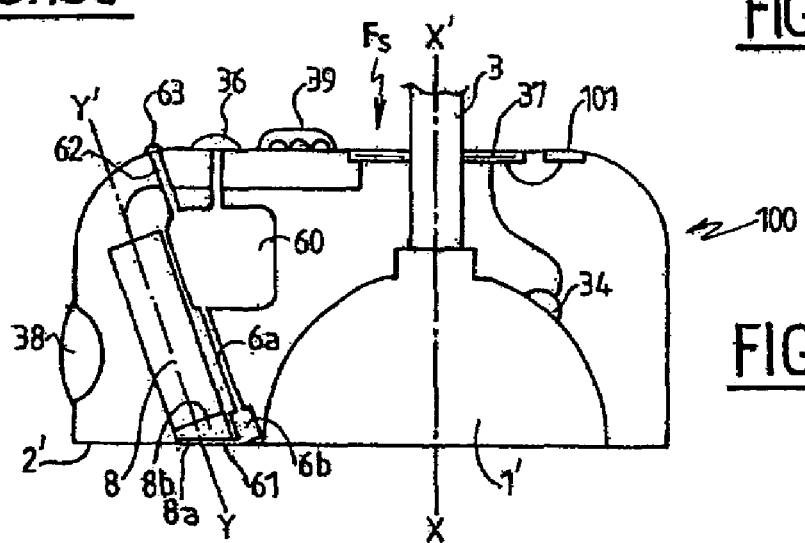
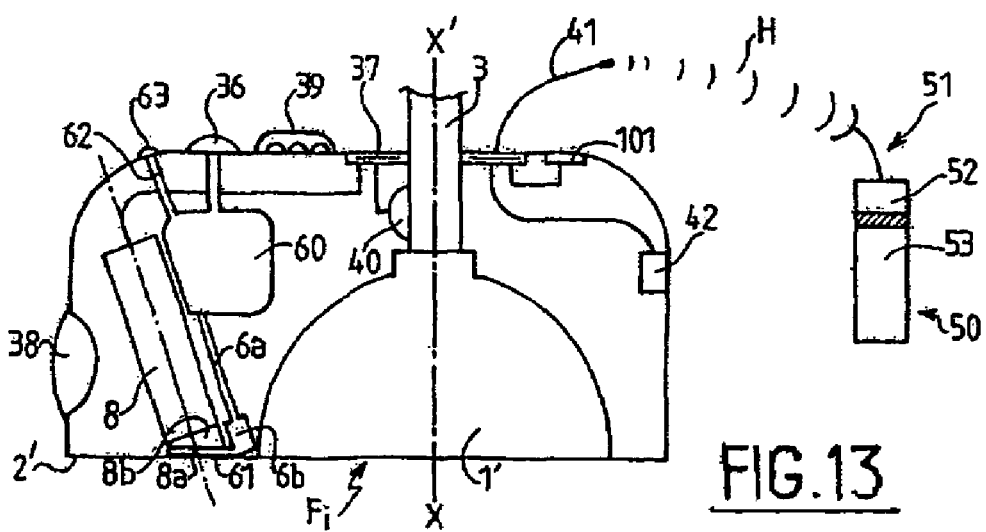

APPARATUS FOR SCREENING AND DIAGNOSING BY DUAL STETHOSCOPIC AND DOPPLER DETECTION

The invention relates to an apparatus for medical screening and diagnosis by dual sound detection, of the stethoscopic type, and ultrasound detection, of the Doppler type. Such an apparatus permits in particular a cross diagnosis by coupling of these detections by auditory and visual analysis. The invention applies to the analysis of arterial pressure, in particular of systolic pressure, and permits, for example, screening of incipient narrowing of the vessels.

Doppler ultrasonography apparatus are presently known which comprise an ultrasound probe equipped with means for emitting ultrasound waves and for receiving these ultrasound waves once they have been reflected by a support, for example the blood flowing through a vessel in the patient. The slowing or acceleration of this flow is manifested by a positive or negative variation in the Doppler ultrasound frequency, by addition or subtraction of a frequency interval of amplitude directly associated with the Doppler effect, hereinafter the "Doppler signal". The measurement of the signal or of this variation can provide reliable information on the caliber of the section of the vessels explored.

In addition to the ultrasound probe, a Doppler ultrasonography apparatus traditionally comprises successive transducer stages permitting detection of the Doppler signal (phase shifter, multiplier, amplifier and filter), a phase comparator attributing a positive or negative character to the Doppler interval detected, an audiofrequency amplifier, and a loudspeaker.

However, the examination performed with the aid of such Doppler apparatus requires specialization, or at least training, in order to acquire and to maintain the practice of interpreting the results obtained. It follows, logically, that this examination is left in the hands of specialists, as the general practitioner is not accustomed to performing this type of examination.

The invention aims to promote Doppler examination so as to permit early screening of cardiovascular diseases, in particular of narrowing of the vessels or incipient arterial disease.

To establish, for example, the presence of incipient arterial disease of the legs, it is necessary to test for a difference between the systolic pressure of the legs and arms of the patient. Such a difference is generally determined by measuring the systolic pressure index (SPI, being the ratio between the systolic pressures of an arm and leg of the patient).

Easier screening of arterial disease of the legs will then encourage an overall evaluation of the arteries, in particular of the coronary and carotid arteries.

Another object of the invention is to provide for dual detection (stethoscopic and Doppler) guaranteeing a high level of coherence between the detections, in order to obtain a diagnosis which is highly reliable.

To achieve these objects, the invention uses means of integrating the Doppler examination in an apparatus having a stethoscope-type structure, forming part of the range of equipment carried by a general practitioner, these means permitting, specifically, convergence of the stethoscopic and Doppler investigations of the same vascular segment (producing a unity of place), with the possibility of providing a dual detection simultaneously (unity of time).

More precisely, the subject of the invention is an apparatus for medical screening and diagnosis by dual detection of stethoscopic and Doppler signals, comprising a sound-transmitting linking conduit connected, at one end, to a housing which at least partially forms an ear trumpet provided with a membrane, and, at the other end, to at least one earpiece for listening to a stethoscopic signal coming from the ear trumpet. In this apparatus, the housing is coupled to at least one ultrasound probe designed to permit convergence of reception of the ultrasonic and stethoscopic signals and connected to a transducer processing circuit capable of supplying, from a Doppler signal, an audio signal, by coupling the processing circuit to a loudspeaker in contact with the ear trumpet for stethoscopic-type listening, and a video signal, by coupling the processing circuit to viewing means for providing visual information.

Thus, the invention makes it possible to obtain simultaneous and localized convergence of the stethoscopic and Doppler investigations without having to move or turn the housing during the examinations. Moreover, the results are communicated with the aid of traditional or standard means, a stethoscope earpiece or a viewing screen, which allows for natural integration of this apparatus in the basic equipment employed by a practitioner.

According to preferred characteristics:

means are provided for delivering and forming a film of semi-solid product on the skin of the patient, in particular a gel, for achieving an intimate contact between skin and housing and for channeling the propagation of the waves; a reservoir of this product, connected to the delivery means, can be advantageously accommodated in the housing;

the loudspeaker is arranged substantially against the ear trumpet so that the audio signal is amplified by the ear trumpet and renders the stethoscopic sound perceptible at the earpiece via the linking conduit, in the same way as in a stethoscope;

a microphone is coupled to the ear trumpet so as to pick up the stethoscopic sound signal and transmit it, in the form of an electrical signal, to the processing circuit and produce a video signal;

the viewing means are in the form of a liquid crystal screen permitting graphic display of a stethoscopic and Doppler signal, or in the form of light-emitting diodes;

a microprocessor is controlled by an interpretation algorithm and coupled to the processing circuit in order to permit analysis and a combination of stethoscopic and/or Doppler measurements, delivered by the processing circuit or else picked up from stethoscopic listening, and to be able to supply a stethoscopic diagnosis, Doppler diagnosis and/or cross diagnosis;

a display module with three light-emitting diodes which is mounted on the housing shows the interpretation and provides a diagnosis based directly on the measurement of the Doppler signal or a cross diagnosis based on the interpretation algorithm by giving preference to the Doppler diagnosis when the interpretations are divergent, each diode emitting in a specific color corresponding, respectively, to a positive diagnosis (existence of a disease), a negative diagnosis (no disease), or a non-interpretable diagnosis (too much doubt regarding the measurements) in the case where the stethoscopic signal is not interpretable, or of malfunction of the apparatus, the diagnosis then being based on the stethoscopic sound signal;

a module for recording and viewing the Doppler or stethoscopic video signal is provided by wireless connection, for example radio or infrared, between the electronic processing circuit and a viewing or printing module;

peripheral outputs are provided in order to permit a connection to a microcomputer or to an audio headset (auxiliary);

for simple use of the probe, in particular with the aid of a finger, an electrical circuit is provided for powering the ultrasound probe, controlled by an actuator which can be mounted on the linking conduit or on the housing;

the actuator is a multifunction switch which serves also for selective control to the means for supplying stethoscopic, Doppler or cross diagnoses by the viewing means, to the means for triggering the diagnosis on the basis of measurements delivered by the processing circuit or else picked up from listening, and to the system for recording and remote viewing;

the multifunction is realized by different stages identified by a decision table or a logic unit for programming the connections of the circuits as a function of the number of times the actuator is activated;

power supply by cell or by rechargeable battery is also provided.

According to a first embodiment, the housing forms an ear trumpet accommodating the ultrasound probe, in particular in a centered manner, and contact means can be interposed temporarily between the ultrasound probe and the membrane of the ear trumpet, in order to transmit a Doppler signal to the processing circuit coupled to the loudspeaker which emits the audio signal amplified in the ear trumpet.

When the ultrasound probe is not in contact with the membrane, a normal stethoscope is available. But when the probe is placed in indirect contact with the membrane, an apparatus of the Doppler type is available.

The means of interposition preferably comprise an inflatable balloon covering the distal end of the probe and a device for inflating the balloon. This inflating device can comprise a tubing which brings the balloon into communication with a source of liquid, and means, preferably comprising a button, intended to drive liquid from the source into the tubing, so as to inflate the balloon.

The control actuator and the button intended to drive liquid are preferably the same button and can be actuated by a finger, and means are provided which are intended to maintain the flow of liquid when the actuation button is released, which means can in particular be an electromagnetic coil applying a magnetic holding force to a plunger, made of magnetic material, for driving back liquid.

Moreover, means for delivering semi-solid product can form a film between the skin and the membrane.

Depending on whether or not the balloon is inflated, a Doppler apparatus or a traditional stethoscope is available. It is thus possible, with the aid of the apparatus functioning as stethoscope, to first determine approximately the anatomical location, for example carotid location, where ultrasonography is to be performed, then carry out the detailed ultrasonography operation at this location which has been determined in advance in an approximate but rapid manner.

It is known that it is desirable, in a Doppler apparatus, to be able to tilt the probe. In this first embodiment, means are advantageously provided which are controlled from outside the ear trumpet and are intended to tilt the probe. These means can comprise a cable, preferably a group of four cables at the four cardinal points of the probe, of which one end is fixed to the end of the probe, and means intended to pull the other end of the cable. The cable, or a part of the set of cables, is pulled so as to tilt the end of the probe in order to orient it toward the sound response most perceptible at the earpiece.

According to a second embodiment, the probe is accommodated in the housing and outside the ear trumpet, the housing forming a substantially cylindrical turret.

The probe can be inclined by a fixed angle of between about 30 and 70 degrees relative to the membrane, preferably between 45 and 55 degrees, in order to optimize the examination by converging the reception of the ultrasound signals and that of the stethoscopic signals.

Advantageously, means of prolongation of the probe are provided in order to compensate for the inclination of the probe. The means for delivery of the semi-solid product then form a connecting layer between the prolongation of the probe and the patient's skin.

According to a preferred characteristic, the linking conduit is connected to the bottom of the ear trumpet, farthest from the membrane, and emerges substantially at the center of the upper face of the turret.

Other advantages and characteristics of the invention will become evident from reading the following description which relates to non-limiting illustrative embodiments and is accompanied by appended figures, in which:

FIGS. 10a and 10b show two perspective views, namely an upper one and a lower one, of a housing of the apparatus according to the invention, in a second embodiment;

FIG. 11 shows a cross-sectional view of the housing according to FIGS. 10a and 10b, in an illustrative embodiment adapted for prioritized processing of the Doppler signal and of the stethoscopic signal in audio mode;

FIG. 13 shows a cross-sectional view of the housing, in an illustrative embodiment adapted for prioritized processing of the Doppler signal and of the stethoscopic signal in video mode;

Figure 1:
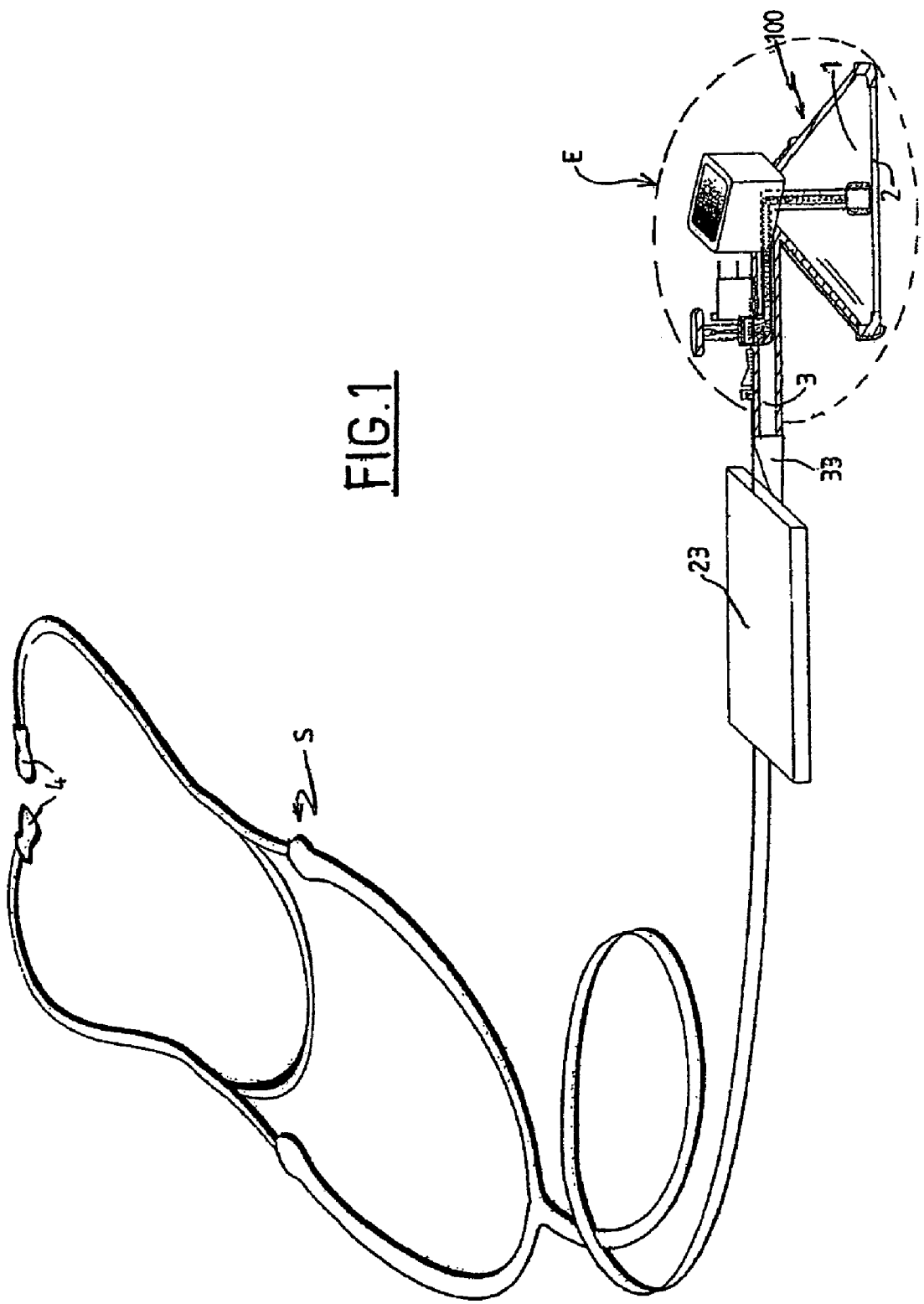
FIG. 1 is an overall view, partially in cross section, of an example of the apparatus according to the invention, in a first embodiment.

The apparatus shown in FIG. 1 comprises a stethoscope endpiece E whose housing 100 is in the form of a conical ear trumpet 1 delimited also by a membrane 2 forming the main base of the ear trumpet, and comprising a linking conduit consisting of a connector 3 and of a flexible tubing 33 communicating with two earpieces 4 in the conventional manner of a stethoscope S, and on which an electrical source 23 is fixed.

Figure 2:
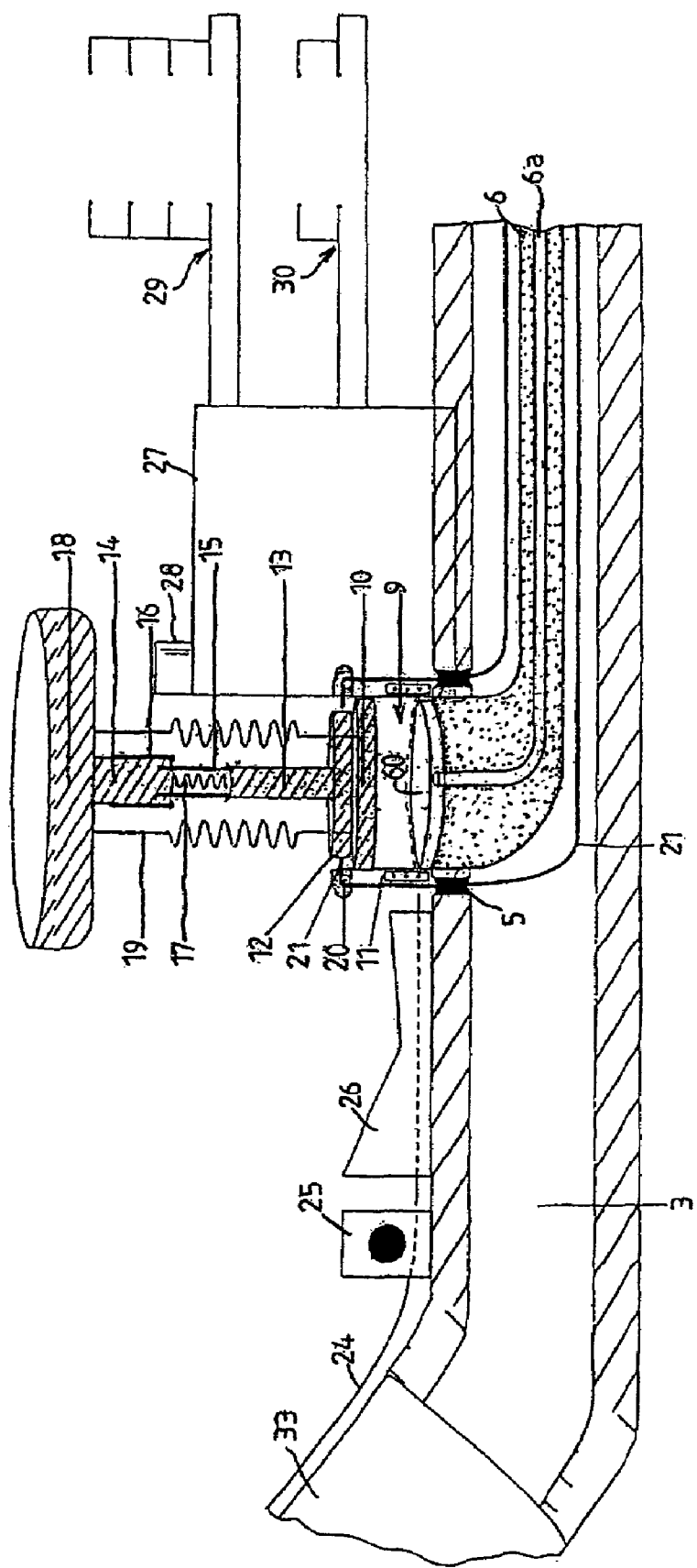
FIG. 2 is a cross-sectional view of a part of the linking conduit of the apparatus in FIG. 1, in which an actuator button and the control circuits are indicated diagrammatically.
Figure 3:
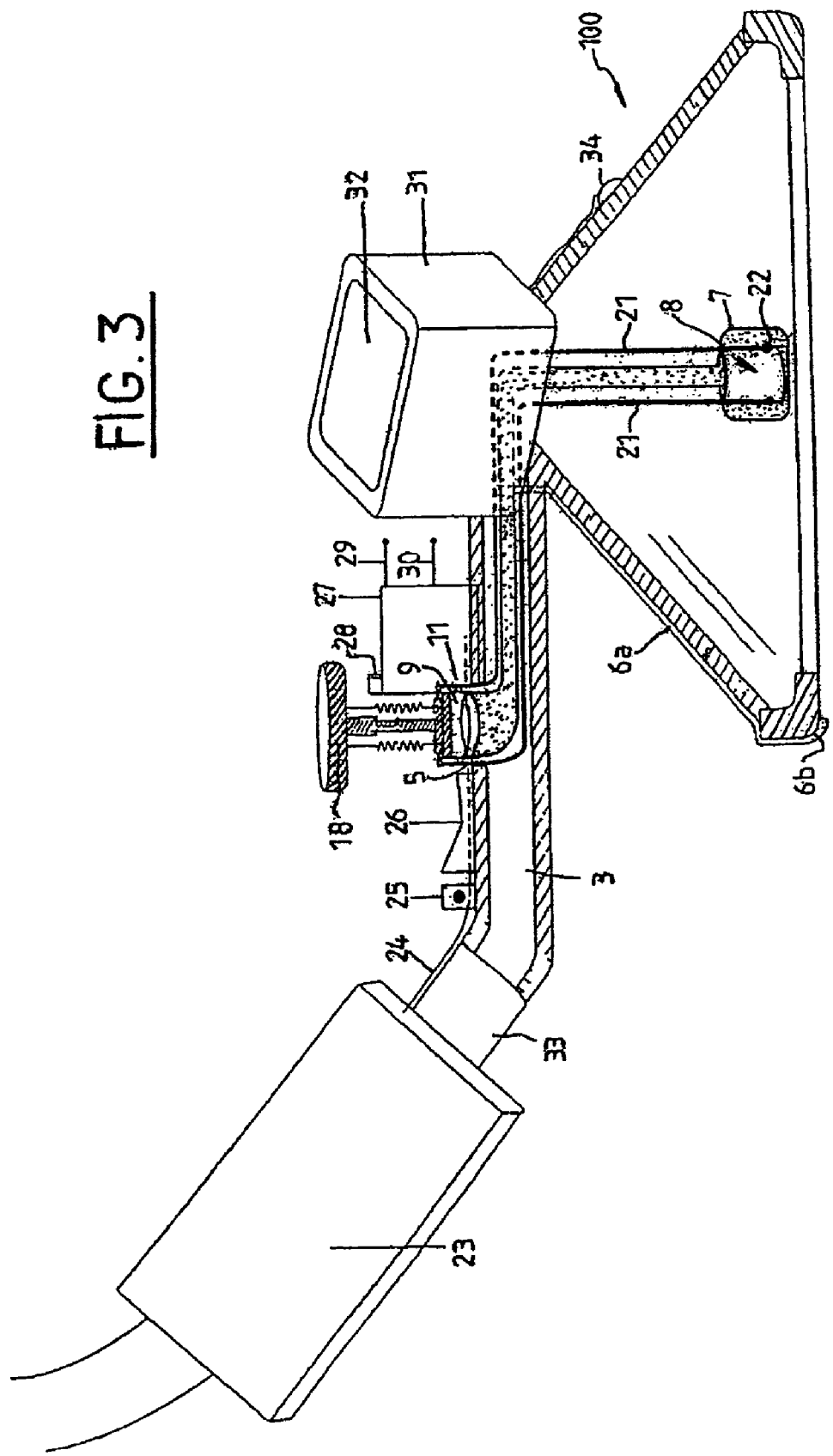
FIG. 3 is a cross-sectional view of the end of this apparatus in the position of stethoscopic functioning.

However, in contrast to a conventional stethoscope, and as is shown more specifically in FIG. 2 and in the overall view of the endpiece in FIG. 3, the connector 3 is provided with a hole 5 which has a sealing insert and into which a tubing 6 passes, opening into a balloon 7 which covers the distal end of an ultrasound probe 8. The tubing 6 is filled with liquid, for example water.

Engaged in the hole 5 there is a cylinder 9 in which a plunger 10 made of magnetic material slides, which plunger 10 is surrounded by an electromagnetic coil 11. The plunger 10 is capped by a disk 12 whose upper face is integral with a rod 13. The rod 13 is mounted telescopically on the rod 14 of an actuator button 18 by way of two rails 15 which can slide on two other rails 16, themselves integral with the rod 14, and a spring 17 is interposed between the opposing faces of the rods 13 and 14. The actuator button 18 is connected to the upper face of the plunger 10 by a spring 19.

A reservoir of gel 60 is arranged in the cylinder 9, between the plunger 10 and the tubing 6. This reservoir is connected to a flexible tube 6a mounted in the tubing 6 then, emerging through sealed orifices in this and in the connector 3, along the conical wall of the ear trumpet 1. The end of the tube 6a is connected to an ejection nozzle 6b situated in contact with the outer face of the membrane 2. Alternatively, the system for distribution of gel and its control means can be mounted independently of the system for inflating the balloon and its control means.

Four pulleys 20, on which four cables 21 run, are fixed to the cylinder 9, and the ends of the cables 21 are fixed at 22 to the probe 8. The other ends of the cables 21 are fixed to the disk 12.

A cell or a rechargeable battery 23 is mounted on the tubing 33 and is connected via a line 24 to a recharging socket 25 and to a switch 26.

The button 18 also controls an electronic processing module 27 via a push button 28 located under the control button 18, so that the latter moves the push button 28 when actuated. The electronic processing module comprises the transducer circuits for conversion of the Doppler signals to audio and video signals.

The electronic processing module 27 is connected to first and second circuits, 29 and 30, for electrical connection in particular to a microprocessor 31 and to an LCD device 32. The first electrical circuit 29 supplies the electromagnetic coil 11, and also the microprocessor and the screen. It powers the probe 8 and a loudspeaker 34 arranged against a wall of the conical ear trumpet 1. The second electrical circuit 30 is a circuit which controls the recording of the Doppler signal by the microprocessor 31 and its display on the device 32.

Figure 4:
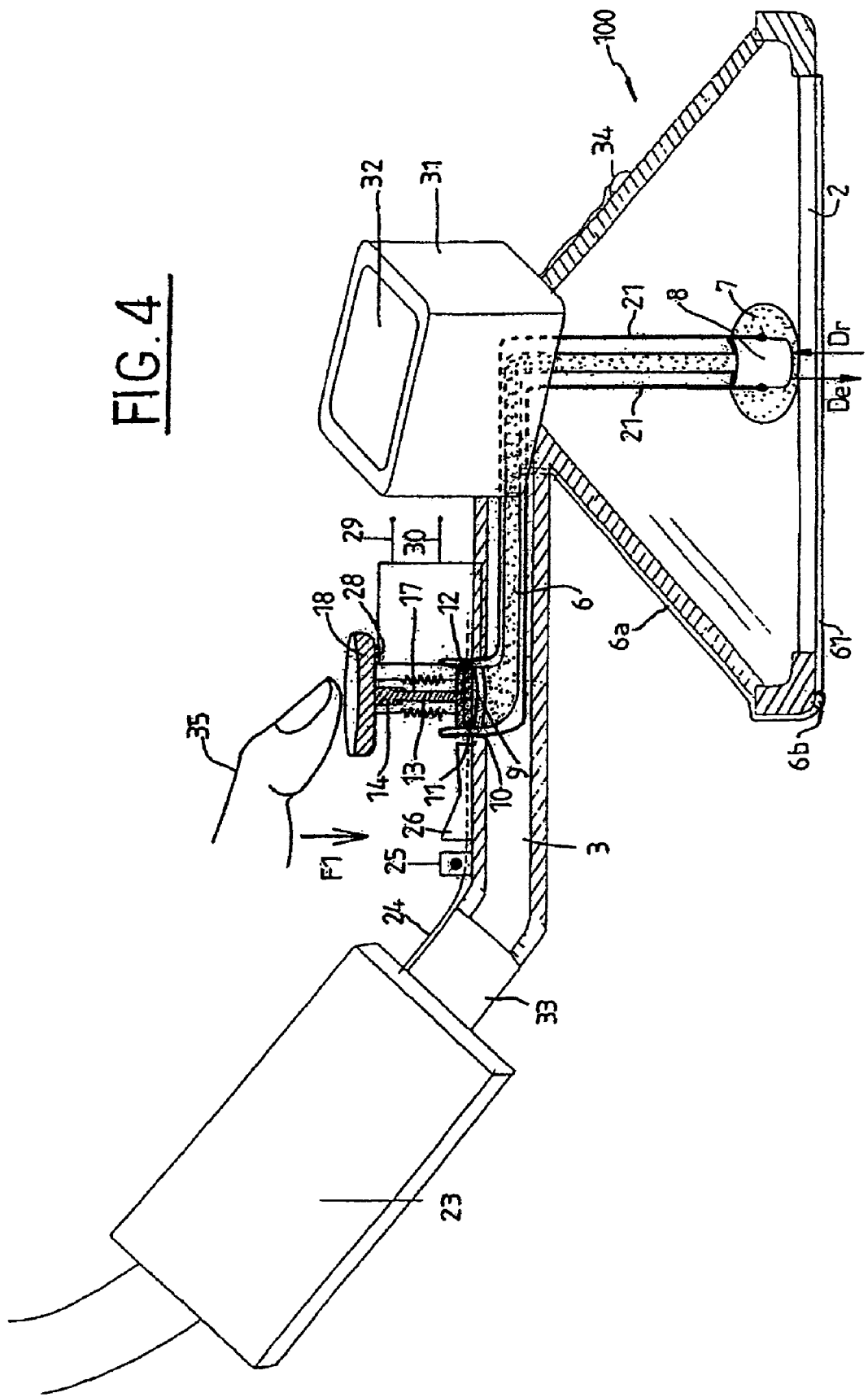
FIGS. 4 and 5 are cross sectional views, in accordance with FIG. 3, in the position of Doppler functioning, in which figures the balloon of the probe is inflated and the probe emits and receives ultrasound waves, and which figures show the engagement and release, respectively, of the actuator button.

The module 27 has a decision table which is such that a first actuation of the button 28, by pressing the actuator 18, takes us to the configuration illustrated in FIG. 4. Having released it, a renewed actuation takes us to the configuration according to FIG. 6. Releasing it again, then actuating it again, takes us to the position in FIG. 8.

The apparatus functions in the following way.

With reference to FIG. 3, in which the balloon 7 is not inflated and the probe 8 is not powered (thumb 35 not active), the apparatus functions as a stethoscope, supplying a stethoscopic audio signal by propagation of the perceptible sound through the membrane 2, the ear trumpet 1 and the flexible conduit 33 to the earpieces 4.

In FIG. 4, the button 18 is activated by the thumb 35 (arrow F1). The finger 14 pushes the rod 13, which itself pushes the disk 12 downwards, causing the plunger 10 to slide in the cylinder 9. The spring 17 is compressed.

The liquid contained in the tubing 6 is driven into the balloon 7 which comes into contact with the membrane 2. The gel 61 is distributed via the nozzle 6b between the membrane 2 and the patient's skin.

At the same time, the button 18 has pushed for the first time on the button 28, so that the first electrical circuit 29 is powered. The electromagnetic coil 11 is powered and maintains the plunger 10 made of magnetic material in place, with the result that the liquid contained in the tubing 6 continues to be driven and the balloon 7 remains inflated. The microprocessor 31 and the screen 32 are powered.

Using piezoelectric elements, the probe 8, which is also powered, emits ultrasounds $D_e$ through the membrane 2 and, in return, receives the reflected ultrasounds $D_r$ supplemented by a Doppler frequency interval to form the Doppler signal. The apparatus then functions as a Doppler ultrasonography apparatus. The Doppler signal is converted by the processing module 27 in order to supply a sound signal by way of the loudspeaker 34. The sound is then amplified in the ear trumpet, propagated through the linking conduit (connector 3 and tubing 33), then listened to at the earpieces 4. It is thus possible to carry out a Doppler examination by stethoscopic listening.

Figure 5:
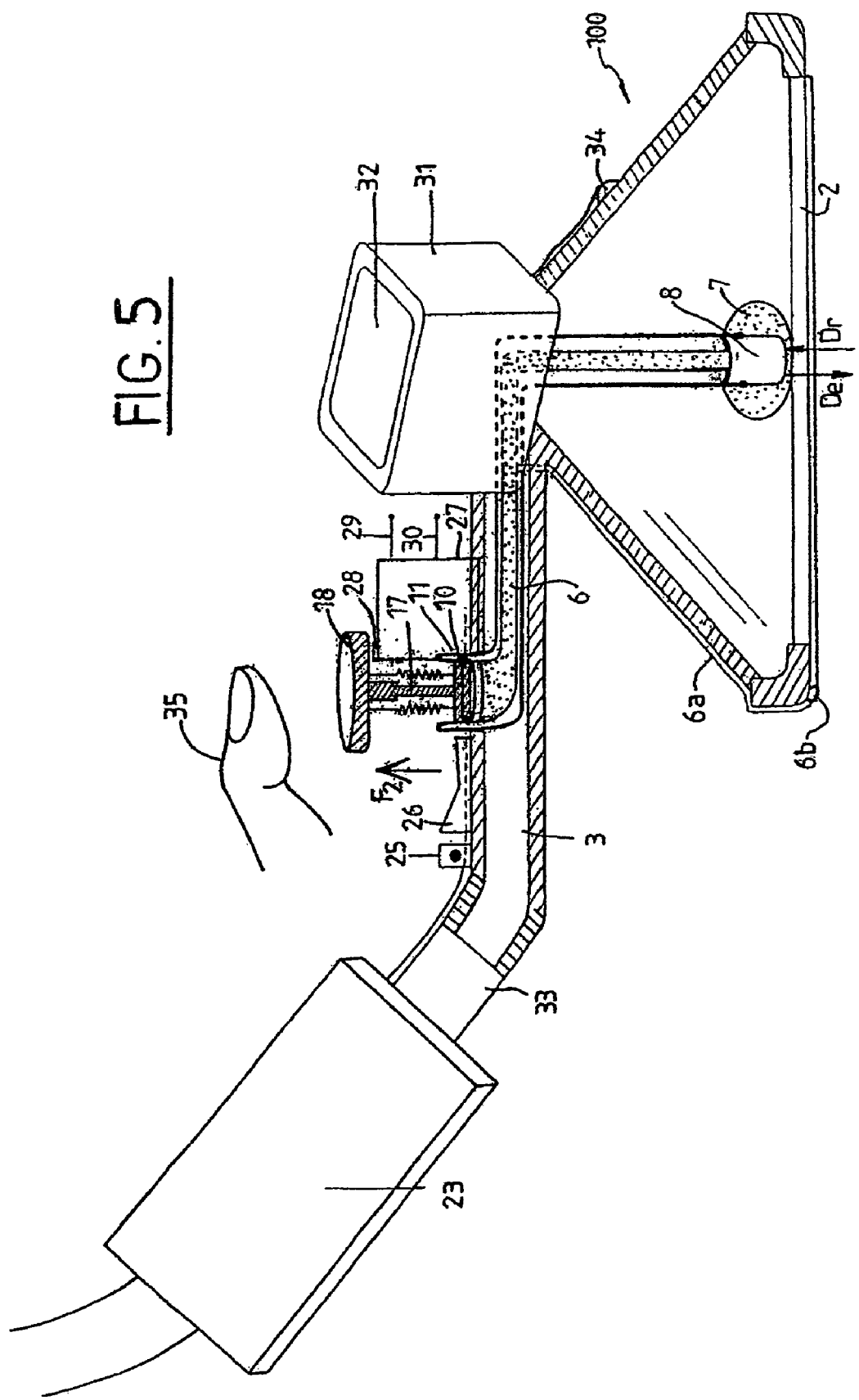

In FIG. 5, the user has stopped pressing the button 18 (arrow F2), but the plunger 10 has remained in position on account of the fact that the coil 11 is powered, and the button 28 is returned upward by the spring 17.

Figure 6:
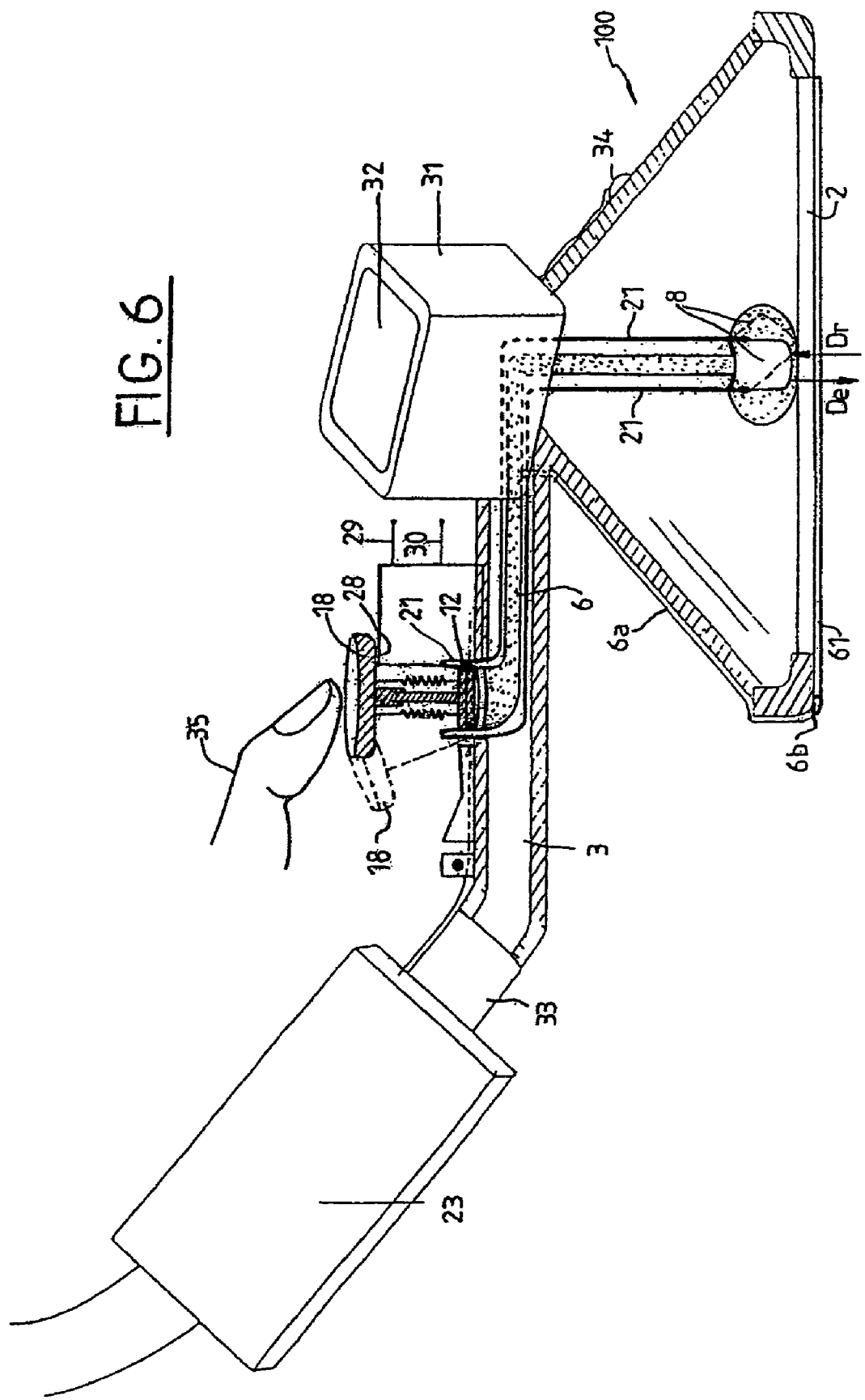
FIGS. 6 through 9 show a view, similar to that in FIGS. 4 and 5, in which the actuator button tilts, in order to optimize the response of the Doppler signal, is then released, and is then actuated again to remove power from all the processing circuits of the apparatus, and is finally released to return to the position for stethoscopic functioning.

In FIG. 6, the broken line shows the button 18 tilted by the thumb 35 in order to optimize the reception of the Doppler signal. This tilting of the button 18 also translates into a tilting of the disk 12. The result of this is that some of the cables 21 are pulled by the disk 12 and cause the end of the probe 8 to tilt. Listening through the earpiece 4, a sound is heard which reaches a maximum at a certain orientation of the button 18 and thus of the probe 8. When this orientation is reached, the button 18 is pressed again while it maintains its orientation. It presses on the button 28, which powers the second circuit 30. The Doppler signal is recorded by the microprocessor 31 and the result is read on the display screen 32.

The microprocessor can be controlled by software for interpreting the Doppler and stethoscopic results. The stethoscopic results are called up by dedicated keys or by the touch-screen. When the results differ, the Doppler result is preponderant in the interpretation. The final diagnosis is displayed in the form of a positive result (disease), a negative result (no anomaly), or a non-interpretable result when the signals are not sufficiently identified or certain. In the case where only the Doppler signal is non-exploitable, the diagnosis is the one (positive or negative) supplied by the stethosocpic signal.

Figure 7:
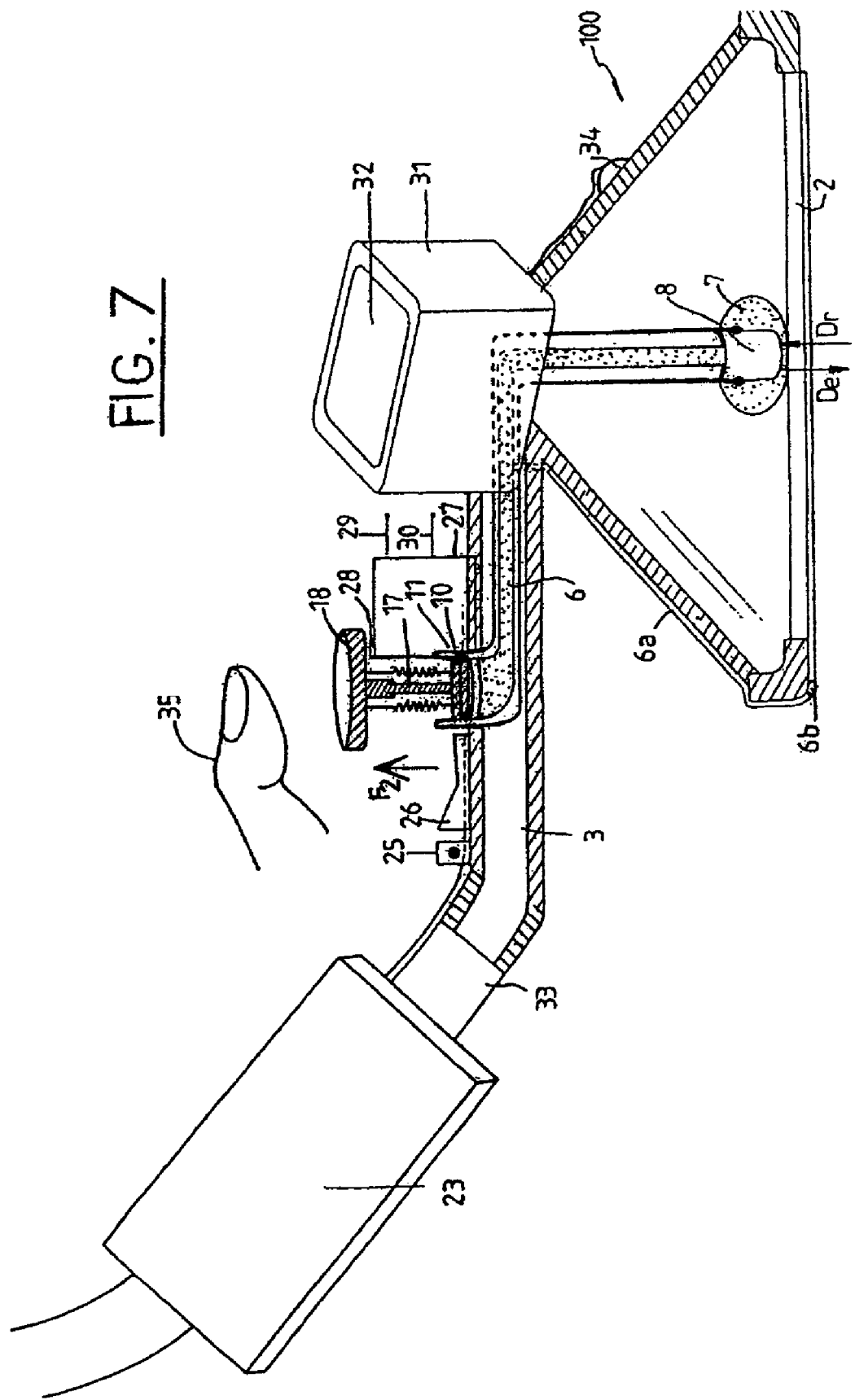
Figure 8:
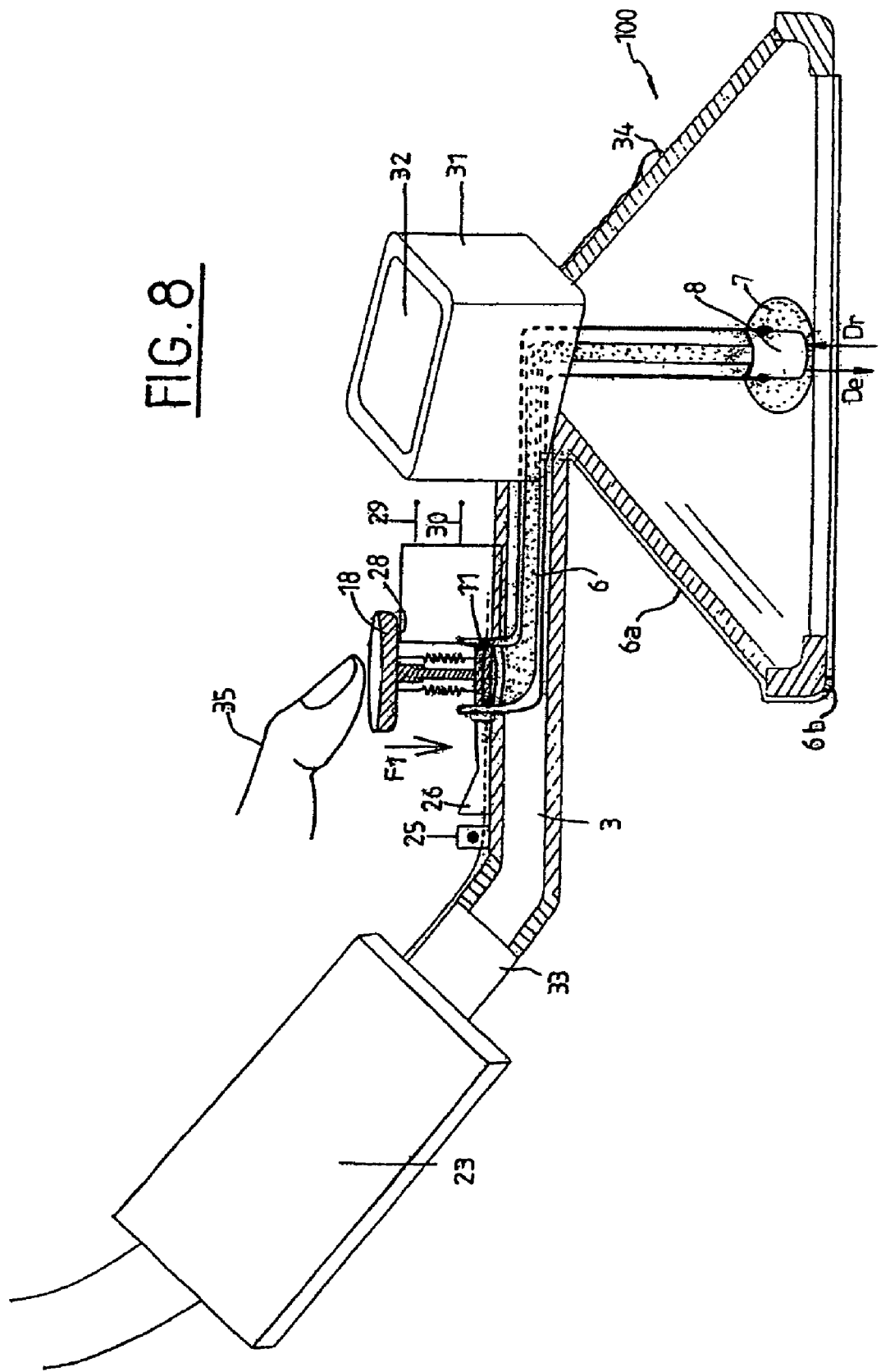

In FIG. 7, the user has stopped pressing the button 18 (arrow F2). The plunger 10 remains held by the electromagnetic coil 11, so that the balloon 7 remains inflated. The recording continues to be displayed on the device 32. In FIG. 8, the button 18 is pressed once again (arrow F1), and this presses the button 28. The first and second circuits 29 and 30 are thus cut and power is removed from the coil 11.

Figure 9:
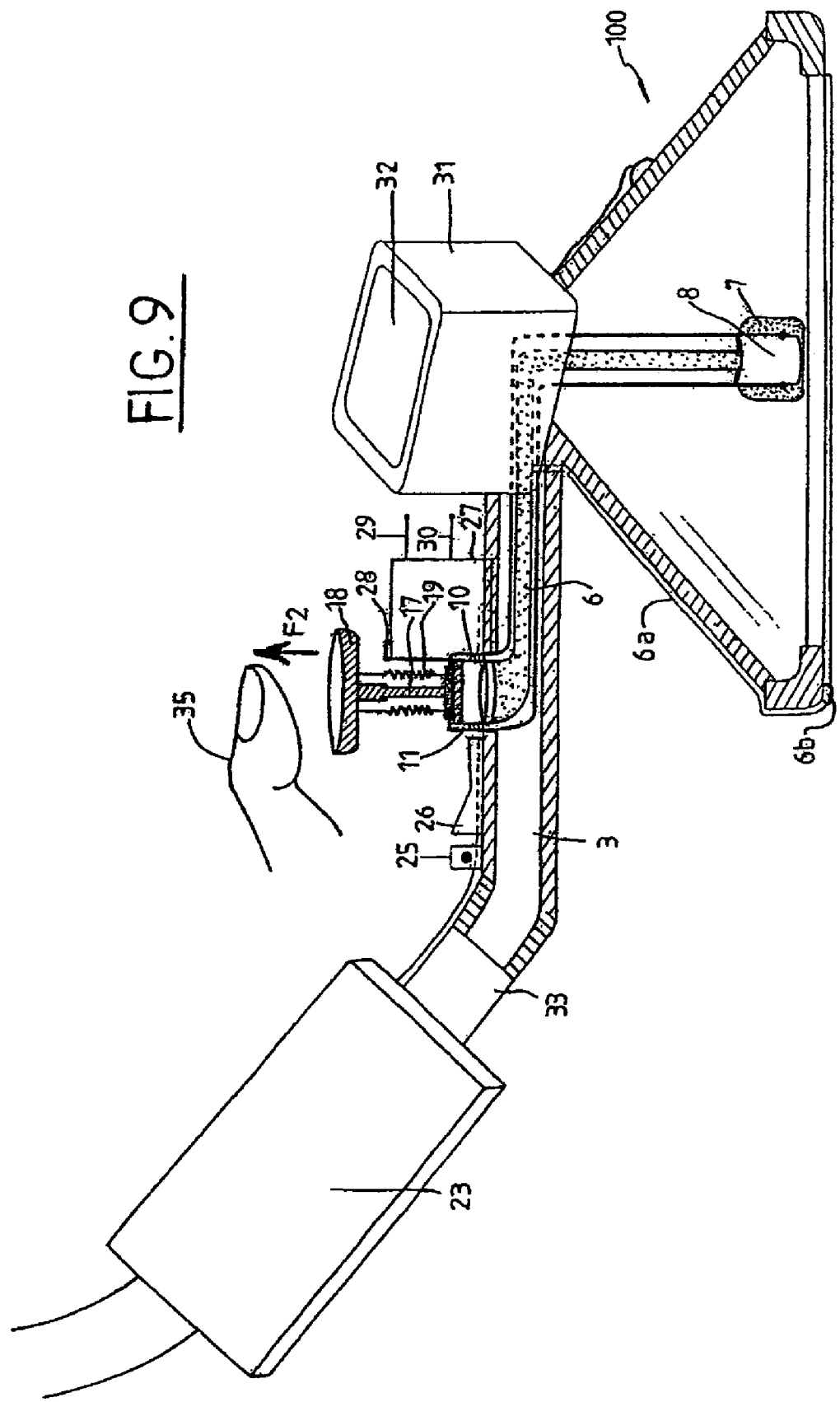

In FIG. 9, the user has stopped pressing the button 18. The plunger 10, which is no longer held by the coil 11, rises under the effect of the springs 17 and 19. The liquid contained in the tubing 6 is aspirated. The balloon 7 deflates. The probe 8 has stopped emitting. If so desired, the switch 26 can be pressed in order to disconnect the whole apparatus, so as to save the cell 23.

FIGS. 10a and 10b show views of an apparatus housing according to the invention in a second embodiment. In this second embodiment, the probe 8 is accommodated in the housing 100, outside of the bell-shaped ear trumpet 1'.

The housing 100 has a turret shape which is substantially cylindrical and of ovoid cross section. The turret is limited by an upper outlet face Fs at the center of which the connector 3 emerges, and by an open lower application face Fi where the flat membrane 2 of the ear trumpet and the end face 8a of a prolongation 8b of the inclined probe 8 are positioned. This prolongation is made of solid or semi-solid material which conducts ultrasound waves, for example silicone gel. In the example illustrated, it has a cylindrical shape with flat end faces cut at suitable angles.

The end face 8a of the prolonged probe is covered by a gel 61 in order to form a continuous connecting layer between the end 8a and the patient's skin. An insulating membrane 2', pierced to keep the end 8a free, can advantageously close the lower face of the turret in order to avoid penetration of the gel inside the turret.

The gel is controlled by a plunger 36 accessible from the upper face Fs. A switch 38 for powering the probe 8 and a display module 39 are also arranged on the housing, the display module being on the upper face Fs in the example illustrated. The switch 38 also serves as a multifunction command, as was described with reference to the first embodiment.

The cross section illustrated in FIG. 11 shows a version which is adapted for priority processing of the signals in audio mode.

The axis Y'Y of the probe is inclined in relation to the central axis X'X of symmetry of the ear trumpet, by a fixed angle of about 50 degrees with respect to the plane of the membrane 2'. This type of inclination permits dual detection by convergence of the Doppler signals and stethoscopic listening downstream of the apparatus, more precisely at the site of investigation.

In this illustrative embodiment, as in the following ones, the gel 61 comes from a reservoir 60 arranged in the housing. The gel is delivered through a flexible tube 6a via an ejection nozzle 6b which is situated in contact with the lower face Fi of the turret. In the case where an insulating membrane 2' is used, the nozzle 6b passes through it via an orifice around which a sealing insert is provided.

The thrust of the plunger 36, mounted telescopically as before, or simply on a restoring spring, makes it possible to meter the appropriate amount of gel delivered via the nozzle. The reservoir can be refilled via a flexible tube 62 which connects the reservoir 60 to a refilling orifice 63 integrated in the housing.

In this same example, the probe 8 is connected to a loudspeaker 34 mounted on an end face of the ear trumpet 1' via the transducer circuit 37. The Doppler signal is converted by the transducer circuit 37 in order to supply an audio signal via the loudspeaker 34. As before, the sound is amplified in the ear trumpet, propagated through the linking conduit 3 and 33, then listened to at the earpieces.

The stethoscopic and Doppler results can be collected and stored, after evaluation by the operator, in interpretation software. This software controls the microprocessor of a microcomputer (not shown) connected to an output 101 provided on the housing 100. Alternatively or in addition to this, the Doppler signal, after conversion by the circuit 37, is also transmitted to the microcomputer and stored in the form of a video signal via the output 101. The microcomputer is equipped with a screen which shows the graph of the Doppler signal.

The basis of the software is an algorithm which supplies a diagnosis based on the evaluations of the listening and of the video Doppler signal. The display module 39 is equipped with three light-emitting diodes. It is mounted on the upper face Fs of the housing 100 and coupled to the transducer circuit 37. This module makes it possible to view the interpretation. The interpretation algorithm gives priority to the Doppler diagnosis when the interpretations are divergent.

The diodes emit in red, orange and green light, respectively:
- the emission of the red diode signifies that the diagnosis is positive (existence of a disease),
- the emission of the green diode signifies that the diagnosis is negative (no disease), and
- the emission of the orange diode signifies that the result is not interpretable, because of measurements which are too "limited".

Figure 12:
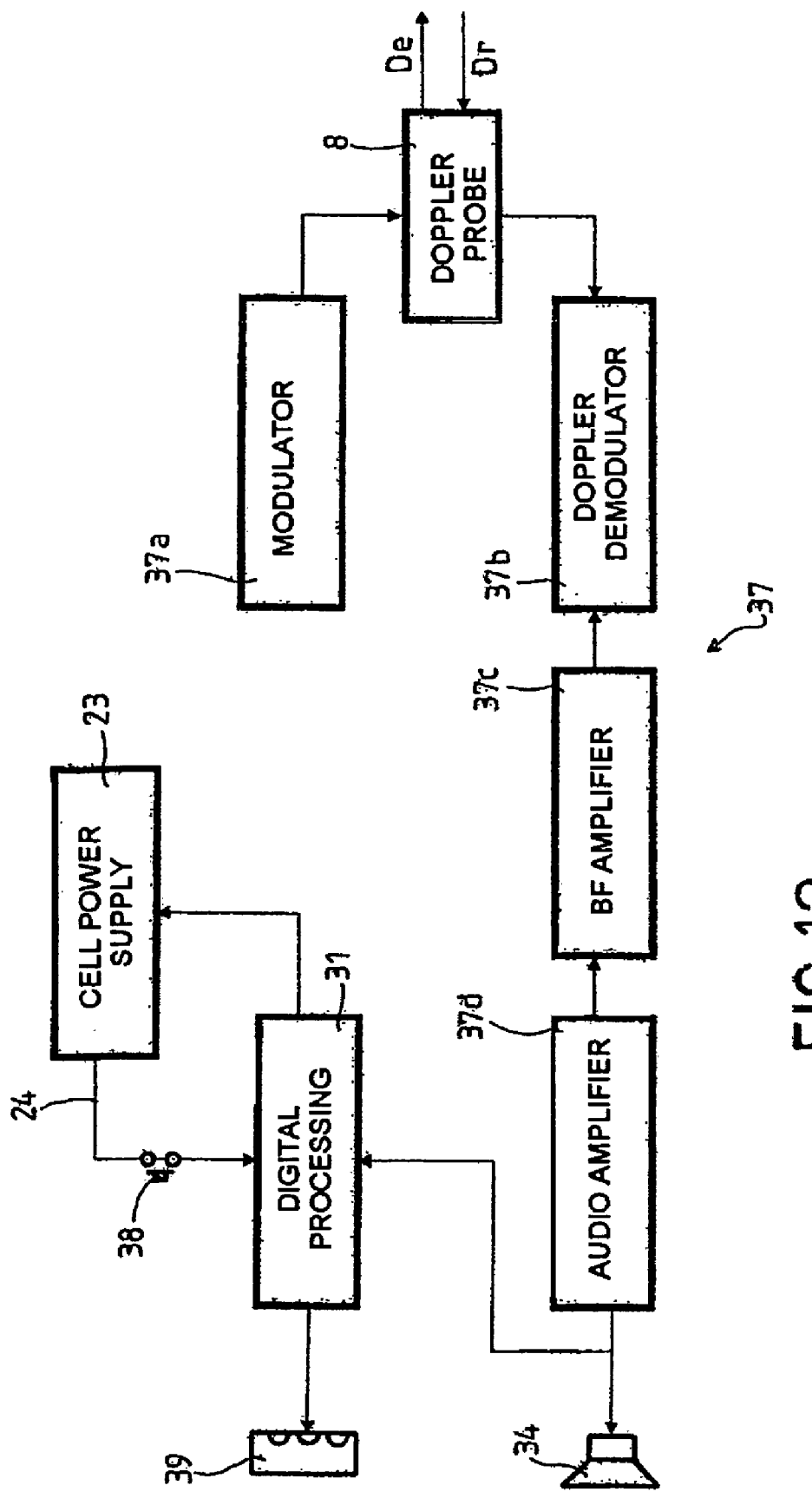
FIG. 12 shows an example of a circuit for processing the Doppler signals of the apparatus according to the invention.

An example of a transponder circuit 37 for processing the Doppler signals is illustrated in FIG. 12. This circuit comprises a modulator 37a for impulsing of the emitted signal $D_e$ at 4 MHz, coupled to the probe 8. The signal received $D_r$ by the probe and to be transmitted to the loudspeaker 34 is processed by the following components in series:
- a low-frequency demodulator 37b, for example for frequencies below 8 kHz;
- an amplifier 37c, for reaching several tens to several hundreds of mV; and
- an audio amplifier 37d, in voltage and impedance.

The signal is transmitted also to the microprocessor for digital processing 31. This microprocessor controls the supply circuit 24 by cell 23 via the switch 38, and also the viewing of the diagnosis by the diode display module 39 described above.

The diodes are triggered by counting the number of impulse fronts received by a Schmidt "trigger" (electronic swivel), making it possible to overcome parasite impulses. For example, in number of fronts per second:
- less than 500 fronts: orange diode (insufficient number: result not interpretable);
- between 500 and 2000 fronts: green diode triggered;
- between 4000 and 8000 fronts: red diode triggered;
- more than 8000 fronts: orange diode (number too high: result not interpretable).

FIG. 13 illustrates more particularly another version of the second embodiment, adapted for priority processing of the signals in video mode. In this example, a microphone 40 is placed against the outer wall of the connector 3. Alternatively, it can be arranged in the linking conduit as long as this position does not cause weakening of the intensity of the direct sound signal, or against the wall of the ear trumpet 1', or more generally at any suitable location situated on the sound path formed by the ear trumpet.

This microphone is able to pick up the stethoscopic sound signal and is connected to the transducer circuit 37 in order to transmit it, in the form of an electrical signal, and produce a video signal at the output. Moreover, the Doppler signal received by the probe 8 is also converted to a video signal.

The video signals are transmitted to a microcomputer, as in the preceding example (illustrated in FIG. 11) via the output 101, and/or to a viewing and printing module 50 situated at a remote point. To this end, an antenna 41 is provided to emit the video signals in radio waves.

A signal H is then picked up by the receiver 51 of the viewing module, then processed in a demodulator 52 and in a viewing adapter 53.

Moreover, a headset output 42 is also provided in this example in order to permit stethoscopic listening based on the sound picked up by the microphone, or on the Doppler signal converted to an audio signal by the circuit 37. The audio headset can be in a conventional form with earpieces 4 of the stethoscope type.

As in the preceding example, the video signals (or audio signals after manual entering of the interpretation by the operator) are evaluated in the interpretation software of the microprocessor or viewed on the screen of the microcomputer.

The display module with three light-emitting diodes 39 permits cross interpretation based on the Doppler and stethoscopic video signals, the Doppler signal being preponderant in the case of divergence.

Figure 14:
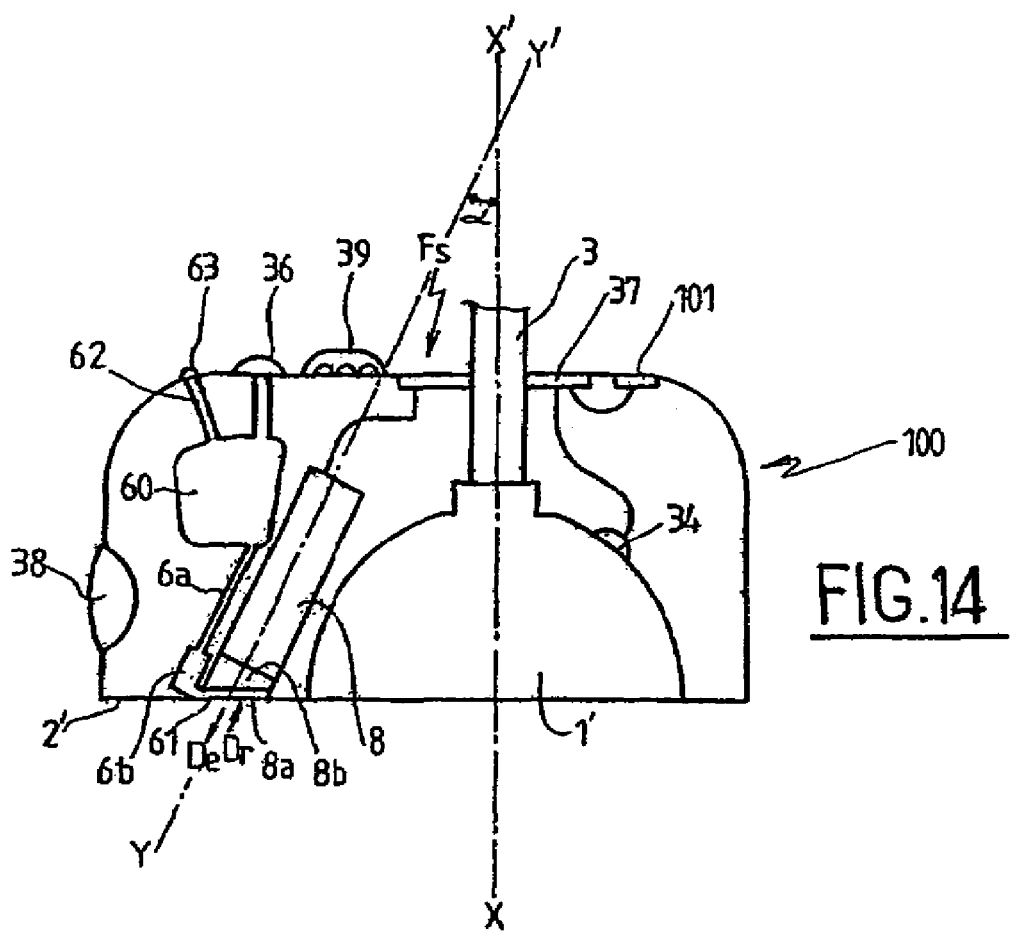
FIG. 14 shows a cross-sectional view of the housing in an alternative embodiment to the preceding example.

The cross section in FIG. 14, which illustrates an alternative embodiment of the housing from FIGS. 11 and 13, shows the probe 8 in an inclined position relative to the central axis X'X, with an inclination opposite to that previously described and illustrated. The convergence of the axis Y'Y of the probe 8 and of the central axis X'X is no longer produced downstream of the housing, as in the previous example, but upstream of the housing 100, in the area of the flexible tubing 33. This solution permits a dual detection which gives priority to the identity of the portion of blood flow, examined successively as a function of its speed, compared to the identity of the investigation site.

Advantageously, an electric micromotor 70 controls the inclination α of a casing 71 into which the probe 8 is slid. The casing and the probe are then driven in rotation about an axis perpendicular to the central axis X'X in such a way as to adjust the angle of inclination α as a function of the received signal, in order to optimize the Doppler investigation.

Figure 15:
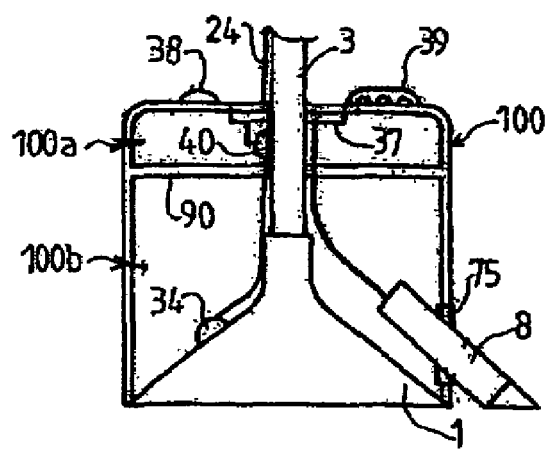
FIGS. 15 and 16 show two other alternatives for clinical validation of a cross sectional view of examples of apparatus according to the invention having a stethoscope-type structure.
Figure 16:
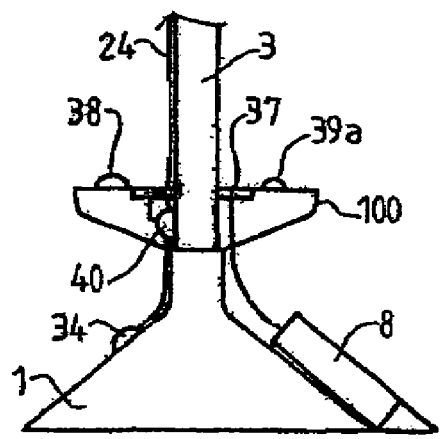

FIGS. 15 and 16 illustrate two other alternative embodiments of clinical validation of the apparatus according to the invention, presenting a simplified structure of stethoscope type.

With reference to FIG. 15, a partition 90 separates the housing 100 into an upper part 100a for signal processing, which comprises the transponder circuit 37, the system of diodes 39 and the switch 38, and a lower part 100b for signal acquisition, in which the microphone 40, the loudspeaker 34, the ear trumpet 1, the supply circuit 24 and the probe 8 ensure the same functions as before.

The housing 100 partially accommodates the probe 8, and a sealing ring 75 is positioned in the cutout of the housing 100 around the probe 8, in order to protect and mechanically insulate the probe. Indeed, the ring allows the probe to be fixed to the housing without disturbing the normal vibrations of the piezoelectric elements of the probe. A Doppler signal of optimal reception is thus obtained.

In a variant of this example, the lower part 100b of the housing can be advantageously curved in its central part in order to promote gripping of the housing of the stethoscope type.

The example in FIG. 16 illustrates a solution even closer to the traditional stethoscope. In this variant, the housing 100 no longer accommodates the probe 8 and is reduced to the upper part 100a for signal processing (FIG. 15). The probe 8 is fixed along the ear trumpet 1 by suitable means known to the person skilled in the art. The system of diodes is reduced to a single diode 39a which is able to successively assume the three colors previously described. This diode can also replace the three-diode system described above in the preceding embodiments.

The invention is not limited to the embodiments described and shown. For example, it is possible, in the second embodiment, for the microprocessor and the viewing module to be arranged as in the first embodiment, or to provide the viewing module with diodes in each example described above.

A second probe can also be accommodated in the housing. Each of the two probes is then dedicated to a particular zone of the body, for example the upper part (arms or neck) and lower part (legs) of the patient. The respective signals of the probes are set at a dedicated frequency, for example 4 and 8 MHz. Other probes can also be provided, the ends of which are for example inscribed in a peripheral crown inside or outside of the ear trumpet. It is then possible to provide an annular envelope in order to form a single annular probe of multiple piezoelectric emitters and receivers.

Moreover, a headset output can also be provided for connecting a headset cable instead of or in addition to the stethoscopic linking conduit, in each example. A system for recording and viewing the Doppler or stethoscopic video signal can be is provided in each embodiment, by wireless connection, for example radio or infrared, between the electronic processing circuit and a viewing or printing module.

The control plunger for the semi-solid product can be accessible from the housing, the switch for powering the probe also being arranged at any suitable location situated on the housing.

Moreover, it is possible to transmit the three types of diagnostic information by vocal synthesis instead of viewing by diodes. The synthetic voice is obtained with the aid of a synthesizer coupled to the microprocessor and is transmitted through the linking conduit to the earpieces for stethoscopic listening.

It is also possible to provide a system for control (oscillometric control or the like) of the charging of the battery, this system being coupled to warning means indicating the need to recharge or replace the battery or the cell when the charge level is below a certain threshold. Such a system can comprise means for turning off the viewing system or interpretation means, so as not to deliver erroneous results when the charge level reaches said threshold.

The invention claimed is:

1. An apparatus for medical screening and diagnosis by dual detection of stethoscopic and Doppler signals, comprising a sound-transmitting linking conduit connected, at one end, to a housing which at least partially forms an ear trumpet provided with a membrane, and, at the other end, to at least one earpiece for listening to a stethoscopic signal coming from the ear trumpet, wherein the housing is coupled to at least one ultrasound probe positioned with a sensing surface co-planar with said membrane to permit converging reception of ultrasonic and stethoscopic signals; and wherein the ultrasound probe is at an angle of about 30-70 degrees relative to the membrane, and is connected to a transducer processing circuit capable of supplying from a Doppler signal, an audio signal by coupling the processing circuit to a loudspeaker for stethoscopic-type listening, and a video signal by coupling the processing circuit to display means, said processing circuit configured to provide converging stethoscopic-type listening and video signal viewing.

2. The apparatus of claim 1, which further comprises means provided for delivering and forming a film of a semi-solid product on the skin of a patient, for achieving an intimate contact between skin of the patient and the housing and for channeling wave propagation.

3. The apparatus of claim 1, wherein the loudspeaker is arranged substantially against the ear trumpet so that the audio signal is amplified by the ear trumpet and renders the stethoscopic sound perceptible at the earpiece by the linking conduit.

4. The apparatus of claim 1, which further comprises a microphone which is coupled to the ear trumpet to detect the stethoscopic sound signal and transmit it, in a form of an electrical signal, to the processing circuit and produce a video signal.

5. The apparatus of claim 1, wherein the display means are in the form of a liquid crystal screen, permitting graphic display of a stethoscopic and Doppler signal, or in the form of a module with light-emitting diodes.

6. The apparatus of claim 1, which further comprises a microprocessor controlled by an interpretation algorithm and coupled to the processing circuit in order to permit analysis and a combination of stethoscopic or Doppler measurements or both, delivered by the processing circuit or detected from stethoscopic listening, and to provide a stethoscopic diagnosis, Doppler diagnosis or cross diagnosis or a combination thereof.

7. The apparatus of claim 1, which further comprises a display module with three light-emitting diodes which is mounted on the housing, which provides an interpretation and a diagnosis based on a measurement of the Doppler signal or a cross diagnosis based on an interpretation algorithm by giving preference to a Doppler diagnosis when the interpretations are divergent, each diode of the module emitting in a specific color corresponding, respectively, to a positive diagnosis, a negative diagnosis, or a non-interpretable result in the case where at least the Doppler measurement is not interpretable.

8. The apparatus claim 7, wherein instead of displaying a non-interpretable result when at least the Doppler measurement is non-interpretable, diagnosis is based on measurement of the stethoscopic signal, each diode of the module emitting in the specific color corresponding, respectively, to a positive diagnosis, a negative diagnosis, or a noninterpretable result; and wherein in a case where the stethoscopic signal is not interpretable, or of malfunction of the apparatus, the diagnosis is based on the stethoscopic sound signal.

9. The apparatus of claim 1, which further comprises, a system of recording and viewing the video signal is provided by wireless connection between the electronic processing circuit and a viewing or printing module.

10. The apparatus of claim 1, which further comprises peripheral outputs in order to permit a connection to a microcomputer and optionally to an audio headset.

11. The apparatus of claim 1, which further comprises for use of the ultrasound probe with aid of a finger, an electrical circuit for powering the ultrasound probe, controlled by an actuator which can be mounted on the linking conduit or on the housing.

12. The apparatus of claim 11, wherein the actuator is a multifunction switch which serves also for selective control of a means for supplying stethoscopic, Doppler or cross diagnoses by the display means, of a means for triggering a diagnosis from measurements delivered by the processing circuit or picked up from listening, and to a system for recording and remote viewing, the multifunction being realized by different stages identified by a decision table or a logic unit for programming the connections of the circuits as a function of the number of times the actuator is activated.

13. The apparatus of claim 1, which further comprises a power supply, which is a cell or rechargeable battery.

14. The apparatus of claim 1, wherein, the housing forms the ear trumpet accommodating the ultrasound probe, in a centered manner, and contact means are provided to be interposed temporarily between the ultrasound probe and the membrane of the ear trumpet, in order to transmit a Doppler signal to the processing circuit coupled to the loudspeaker which emits the audio signal amplified in the ear trumpet.

15. The apparatus of claim 14, wherein the contact means of interposition comprises an inflatable balloon covering a distal end of the ultrasound probe and a device for inflating the balloon with liquid.

16. The apparatus of claim 15, wherein the inflating device comprises a tubing which brings the balloon into communication with a source of liquid, and means configured to drive liquid from the source into the tubing.

17. The apparatus of claim 15, wherein the contact means of interposition between the ultrasound probe and the membrane is controlled from outside the ear trumpet by an actuator button.

18. The apparatus of claim 17, wherein the contact means controlled from outside the ear trumpet further comprises means to tilt the ultrasound probe and is provided in connection with the actuator button.

19. The apparatus of claim 18, wherein the means to tilt the probe comprises at least one cable, of which one end is fixed to the end of the ultrasound probe, and means configured to pull the other end of the cable and tilt the end of the probe in order to orient it toward the sound response most perceptible at the earpiece.

20. The apparatus of claim 18, wherein the actuator button and the contact means provide a flow of liquid when the actuator button is released, the means comprising a plunger made of a magnetic material for driving the liquid, and an electromagnetic coil applying a magnetic force for holding a plunger.

21. The apparatus of claim 17, which further comprises a circuit which powers the ultrasound probe and which is controlled by the actuator button.

22. The apparatus of claim 17, which further comprises a circuit which records the Doppler signal and which is controlled by the actuator button.

23. The apparatus of claim 1, wherein the ultrasound probe is accommodated in the housing and outside the ear trumpet, the housing forming a substantially cylindrical turret.

24. The apparatus of claim 23, in which, the ultrasound probe is inclined toward the central axis of the ear trumpet by an angle between about 40 and 55 degrees.

25. The apparatus of claim 23, in which, the housing has an ovoid cross section, wherein the turret is limited by an upper face, at the center of which the linking conduit emerges, and by an open lower face where the membrane of the ear trumpet and the end of the probe are positioned.

26. The apparatus of claim 25, which further comprises a plunger which controls a semi-solid product and is accessible from the housing, in particular from the upper face, a switch for powering the ultrasound probe also being arranged on the housing.

27. The apparatus of claim 26, which further comprises a reservoir arranged in the housing, gel being delivered through a flexible tube by an ejection nozzle situated in contact with the lower face of the turret, and a thrust of the plunger making it possible to dose the correct quantity of gel delivered via the nozzle.

28. The apparatus of claim 23, wherein the ultrasound probe is prolonged, and means are provided for delivering a semi-solid product forming a connecting layer between the end of the continuation of the ultrasound probe and the skin of the patient.

29. The apparatus of claim 23, wherein the ultrasound probe is connected to a loudspeaker, mounted on an outer face of the ear trumpet by a transducer circuit, the Doppler signal is converted by the transducer circuit in order to supply an audio signal by the loudspeaker, the sound being amplified in the ear trumpet, propagated in the linking conduit, then listened to at the earpieces.

30. The apparatus of claim 29, which further comprises interpretation software which controls a microprocessor of a microcomputer coupled to an output provided on the housing comprising means for retrieving and storing results of stethoscopic or Doppler listening or both.

31. The apparatus of claim 30, wherein the microcomputer is equipped with a screen which shows the graph of the Doppler signal after the Doppler signal has been converted by the circuit and also transmitted to the microcomputer and stored in the form of a video signal via the output.

32. The apparatus of claim 30, wherein the interpretation software provides a diagnosis on a basis of evaluations which have been retrieved and stored, with a display nodule with at least one light emitting diode, which is mounted on the housing and coupled to the transducer circuit for viewing the interpretation.

33. The apparatus claim 1, wherein the ultrasound probe is accommodated partially in the housing and partially outside the housing, the ultrasound probe passing through the housing by means of a sealing ring which mechanically isolates the ultrasound probe.

34. The apparatus of claim 33, wherein the housing has a lower part curved in its central area.

35. The apparatus of claim 1, wherein the ultrasound probe is outside the housing, which is reduced to an upper part for signal processing, the ultrasound probe being fixed along the ear trumpet.

36. The apparatus of claim 1, which further comprises a display module for viewing and printing situated at a remote point, which receives video signals.

37. The apparatus of claim 36, which further comprises an antenna to emit video signals picked up by a receiver of the display module, for further processing in a demodulator and in a viewing adapter.

38. The apparatus of claim 36, which further comprises a headset output to permit stethoscopic listening basal on the sound or based on the Doppler signal converted into an audio signal.

39. The apparatus of claim 36, wherein the video signals, or audio signals or both, after pickup, are transmitted to a microprocessor for evaluation and are displayed on the screen of a microprocessor.

40. The apparatus of claim 36, further comprising the display module with light-emitting diodes showing a direct or cross interpretation based on the Doppler and stethoscopic video signals.

41. The apparatus of claim 2, wherein the semi-solid product is in a form of a gel.

42. A method of effecting medical screening and diagnosis, which comprises providing the apparatus of claim 1; positioning the apparatus on a subject; and detecting both stethoscopic and Doppler signals to effect said screening and diagnosis.

43. The method of claim 42, further comprising establishing a Systolic Pressure Index (SPI).

44. The method of claim 43, further comprising determining whether the subject has an incipient arterial disease.

45. The method of claim 44, wherein the arterial disease is of coronary or carotid arteries or both.

* * * * *